(12) United States Patent
Muraki

(10) Patent No.: US 8,613,890 B2
(45) Date of Patent: Dec. 24, 2013

(54) MICROPARTICLE SORTING APPARATUS, FLOW CYTOMETER USING THE SAME AND MICROPARTICLE SORTING METHOD

(75) Inventor: Yosuke Muraki, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/847,103

(22) Filed: Jul. 30, 2010

(65) Prior Publication Data
US 2011/0033339 A1      Feb. 10, 2011

(30) Foreign Application Priority Data

Aug. 6, 2009 (JP) ................................. 2009-183107

(51) Int. Cl.
*G01N 15/06* (2006.01)
*G01N 33/00* (2006.01)
*G01N 33/48* (2006.01)

(52) U.S. Cl.
USPC ............... 422/68.1; 422/50; 422/62; 422/63; 422/81; 422/82; 436/43; 436/174; 436/180

(58) Field of Classification Search
USPC ............. 422/50, 68.1, 62, 63, 81, 82; 436/43, 436/174, 180
See application file for complete search history.

(56) References Cited

U.S. PATENT DOCUMENTS

| | | | |
|---|---|---|---|
| 5,643,796 A * | 7/1997 | Van den Engh et al. | 436/50 |
| 7,232,687 B2 | 6/2007 | Lary | |
| 2005/0227362 A1* | 10/2005 | Lary et al. | 436/63 |

FOREIGN PATENT DOCUMENTS

| | | |
|---|---|---|
| JP | 60-122864 | 7/1985 |
| JP | 60-122864 | 8/1985 |
| JP | 62-151742 | 7/1987 |
| JP | 62-167478 | 7/1987 |
| JP | 10-507525 | 7/1998 |
| JP | 10-507526 | 7/1998 |
| JP | 2002-505423 | 2/2002 |
| JP | 2002-0521658 | 7/2002 |
| JP | 2006-162264 | 6/2006 |
| JP | 2006-170687 | 6/2006 |
| JP | 2007-532874 | 11/2007 |
| JP | 2009-154147 | 7/2009 |

OTHER PUBLICATIONS

Japanese Office Action issued May 14, 2013 in corresponding Japanese Patent Application No. 2009-183107.
Japanese Office Action issued Sep. 3, 2013 in corresponding Japanese Patent Application No. 2009-183107.

* cited by examiner

*Primary Examiner* — Brian J Sines
(74) *Attorney, Agent, or Firm* — K&L Gates LLP

(57) ABSTRACT

Disclosed herein is a microparticle sorting apparatus, including: a discharge direction confirming section configured to confirm a discharge direction of a discharged liquid discharged from a discharge outlet of a flow path; opposite electrodes disposed downstream with respect to the discharge outlet; an opposite electrode position controlling section configured to control positions of the opposite electrodes in accordance with the discharge direction confirmed by the discharge direction confirming section; a droplet generating section configured to generate a droplet from the discharge outlet; and a charging section configured to electrically charge the droplet with electric charges.

5 Claims, 8 Drawing Sheets

MICROPARTICLE SORTING APPARATUS, FLOW CYTOMETER USING THE SAME AND MICROPARTICLE SORTING METHOD

CROSS REFERENCES TO RELATED APPLICATIONS

The present application claims priority to Japanese Priority Patent Application JP 2009-183107 filed in the Japan Patent Office on Aug. 6, 2009, the entire content of which is hereby incorporated by reference.

BACKGROUND

The present application relates to a microparticle sorting apparatus, a flow cytometer using the same, and a microparticle sorting method, and more particularly to a microparticle sorting apparatus for sorting microparticles caused to flow within a flow path, a flow cytometer using the same, and a microparticle sorting method.

In recent years, along with the development of an analyzing technique, a technique is being developed with which microparticles or the like such as biological microparticles such as a cell and a microorganism, and micro-beads are caused to flow within a flow path, the microparticles are individually measured in a process for causing the microparticles to flow within the flow path, and the microparticles thus measured are analyzed and sorted. A technical improvement in an analyzing technique called a flow cytometry rapidly advances as a typical example of such a technique for analyzing or sorting the microparticles using the flow path.

The flow cytometry means an analyzing technique with which the microparticles as an object of an analysis are drawn up in a fluid, and in this state, are poured into a flow path, and fluorescences or scattered lights generated from the microparticles are detected by radiating a laser beam or the like to the microparticles, thereby analyzing and sorting the microparticles.

Although with the flow cytometry, the microparticles after completion of the various kinds of measurements for the microparticles are separated from one another and retrieved in accordance with the measurement results in such a manner, the following method is generally used as a concrete method.

For example, when a sample flow containing therein microparticles is discharged from a flow path, a droplet containing therein the microparticles is generated by using an ultrasonic generator, and plus or minus electric charges are added to the droplet thus generated. Also, the droplet is held between two sheets of deflecting plates across which a potential difference is developed in the middle of the dropping, and the droplet containing therein the microparticles thus electrically charged is drawn to one of the two sheets of deflecting plates in accordance with the electric charges, thereby sorting the microparticles.

The technique for analyzing and sorting the microparticles within the flow path such as the flow cytometry is widely utilized in the various kinds of fields such as a medical field, a drug-discovery field, a clinical laboratory field, a food field, an agriculture field, an engineering field, a forensic medicine field, and a criminal identification field. In particular, in the medical field, the analyzing and sorting technique plays an important part in a pathology, a tumor immunology, transplantation studies, a genetics, a regenerative medicine, a chemical care, and the like.

Thus, the technique for analyzing and sorting the microparticles within the flow path is necessary for the very wide field. Also, a technique relating to a sorting process progresses in development day and day. For example, JP-T-2007-532874 proposes a method of controlling an actuation of a flow cytometer with which a subsidiary illumination and a detection unit are disposed in each of a position of a break-off point of a droplet, and a downstream position of the break-off point, thereby making it possible to confirm whether or not the droplet is sorted in an intended flow path.

Although the various kinds of techniques are proposed in the process for sorting the microparticles in such a manner, for the purpose of precisely sorting the microparticles, it is very important to control an initial discharge direction when the microparticles are discharged from the flow path. In particular, in recent years, a flow path formed within a substrate made of a plastic, a glass or the like is used, or a mass-produced flow path is used in many cases. Therefore, a dispersion is caused in the discharge direction in many cases unless a shape of an outlet of the flow path is precisely processed.

For example, FIG. 9 is a photograph substituted for a drawing when a flow path formed in a plastic substrate is viewed from a direction of a flow path outlet (discharge outlet). As shown in FIG. 9, the discharge outlets have the various kinds of shapes. Thus, it is really difficult to control the precise of the shape of the discharge outlet in a cutting work in a phase of mass-production. The control of the shape precise of the discharge outlet is generally very expensive.

There is expected a method of causing the sample or the like to flow within each of the flow paths before shipping to confirm the discharge direction. However, the treatment such as sterilization is carried out in advance for the flow path used in the sorting of the microparticles in many cases. Thus, it may be impossible to cause the sample to flow within the flow path before the shipping in many cases.

SUMMARY

As described above, it is very important to control the initial discharge direction when the microparticles are discharged from the flow path in the process for sorting the microparticles. However, as with the flow path recently used, in the flow path formed within the plastic or glass substrate, or in the mass-produced flow path, it may be really impossible to control the precision of the shape of the discharge outlet.

In the process for sorting the microparticles, for example, when as shown in FIG. 10A, the sorting is carried out by using opposite electrodes 13a and 13b for sorting, it is preferable that a droplet D discharged from a flow path 11 passes through a center portion between the opposite electrodes 13a and 13b. However, when the discharge outlets of the flow paths 11 have the various kinds of shapes as shown in FIG. 9, a pathway of the droplet D diverges sharply from the central portion between the opposite electrodes 13a and 13b as shown in FIG. 10B in some cases. In such cases, it may be impossible to precisely sort the droplet D in a desired direction by using the opposite electrodes 13a and 13b.

The present application has been made in order to solve the problems described above, and it is therefore desirable to provide a microparticle sorting apparatus which is capable of precisely sorting microparticles even when a flow path having a discharge outlet having any shape is used, a flow cytometer using the same, and a microparticle sorting method.

In order to attain the desire described above, according to an embodiment, there is provided a microparticle sorting apparatus including: discharge direction confirming means for confirming a discharge direction of a discharged liquid discharged from a discharge outlet of a flow path; opposite electrodes disposed downstream with respect to the discharge outlet; opposite electrode position controlling means for controlling positions of the opposite electrodes in accordance with the discharge direction confirmed by the discharge direction confirming means; droplet generating means for generating a droplet from the discharge outlet; and charging means for electrically charging the droplet with electric charges.

According to another embodiment, there is provided a flow cytometer including: discharge direction confirming means for confirming a discharge direction of a discharged liquid discharged from a discharge outlet of a flow path; opposite electrodes disposed downstream with respect to the discharge outlet; opposite electrode position controlling means for controlling positions of the opposite electrodes in accordance with the discharge direction confirmed by the discharge direction confirming means; light radiating means for radiating a light to microparticles being caused to flow within the flow path; optical detecting means for detecting optical information generated from the microparticles by the radiation of the light by the light radiating means; droplet generating means for generating a droplet containing therein the microparticles from the discharge outlet; and charging means for electrically charging the droplet with electric charges in accordance with the optical information detected by the optical detecting means.

According to still another embodiment, there is provided a microparticle sorting method including the steps of: causing a control liquid to flow through a flow path having a discharge outlet provided therein; confirming a discharge direction of the control liquid discharged from the discharge outlet; controlling positions of opposite electrodes disposed downstream with respect to the discharge outlet in accordance with the discharge direction confirmed in the step of confirming the discharge direction; causing microparticles to flow through the flow path; generating a droplet containing therein the microparticles from the discharge outlet; electrically charging the droplet with electric charges; and applying a voltage across the opposite electrodes.

Here, the technical terms used in the present application are defined as follows. "The microparticles" described in the present application mean all biologically-relevant microparticles such as a cell, a mioorganism, a liposome, a DNA and a protein, or synthetic particles such as a latex particle, a gel particle and an industrial particle as long as they are matters each of which can be caused to flow within the flow path.

According to the present application, since the microparticle sorting apparatus is provided with the opposite electrode position controlling means, the positions of the opposite electrodes can be changed in accordance with the various kinds of discharge directions. For this reason, the microparticles can be precisely sorted even when the flow path having the outlet having any shape is used.

Additional features and advantages are described herein, and will be apparent from the following Detailed Description and the figures.

DETAILED DESCRIPTION

The present application will be described in detail below with reference to the drawings according to an embodiment.
1. Microparticle Sorting Apparatus 1
(1) Flow Path 11
(2) Discharge Direction Confirming Section 12
(3) Opposite Electrodes 13a and 13b
(4) Opposite Electrode Position Controlling Section 14
(5) Droplet Generating Section 15
(6) Charging Section 16
(7) Acceptor 17
(8) Acceptor Position Controlling Section 18
2. Flow Cytometer 10
(1) Light Radiating Section 19
(2) Optical Detecting Section 20
3. Microparticle Sorting Method 100
(1) Process I for Causing Control Liquid to Flow
(2) Discharge Direction Confirming Process II
(3) Opposite Electrode Position Controlling Process III
(4) Process IV for Causing Microparticles to Flow
(5) Droplet Generating Process V
(6) Charging Process VI
(7) Voltage Applying Process VII
(8) Acceptor Position Controlling Process VIII
(9) Light Radiating Process IX
(10) Optical Detecting Process X
1. Microparticle Sorting Apparatus 1

Figures 1A, 1B:
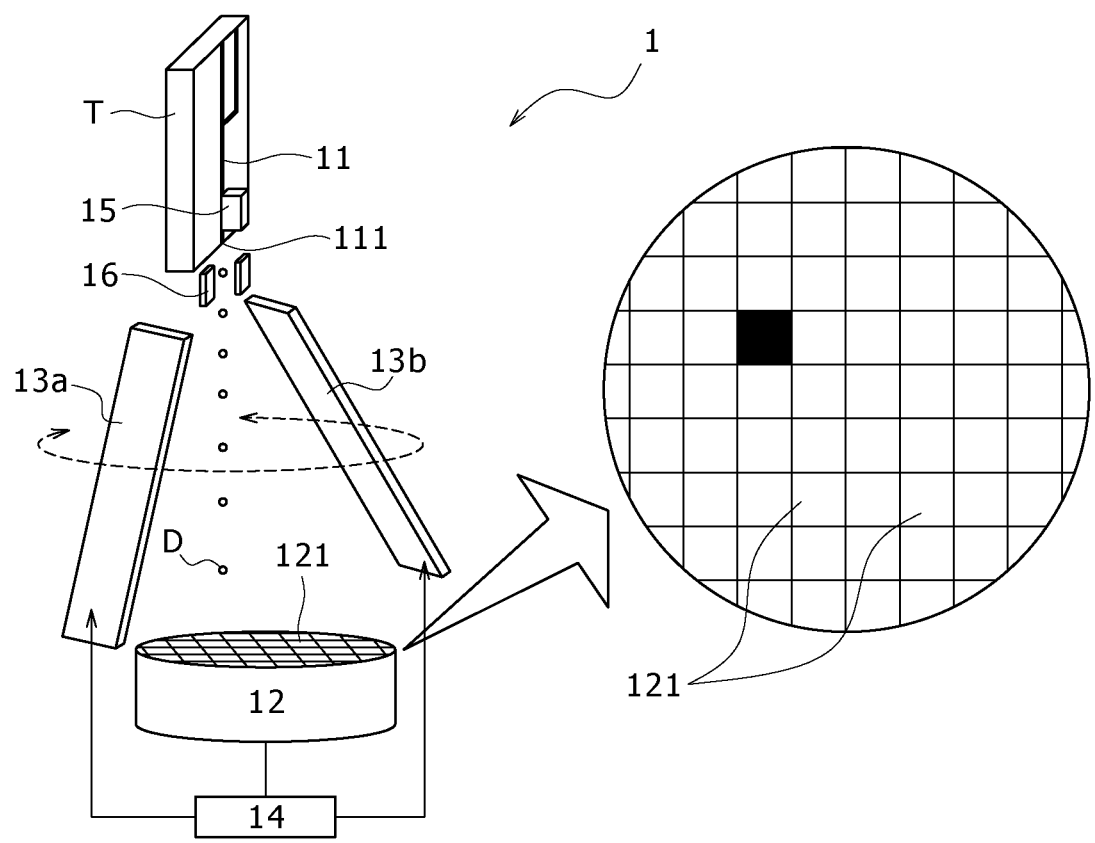
FIGS. 1A and 1B are respectively a schematic conceptual view schematically showing a microparticle sorting apparatus according to a first embodiment, and a top plan view of a discharge direction confirming section of the microparticle sorting apparatus shown in FIG. 1A.

FIGS. 1A and 1B are respectively a schematic conceptual view schematically showing a microparticle sorting apparatus 1 according to a first embodiment, and a top plan view of a discharge direction confirming section 12 of the microparticle sorting apparatus 1 shown in FIG. 1A. The microparticle sorting apparatus 1 is an apparatus which can sort microparticles discharged from a flow path 11 having a discharge outlet 111 adapted to adopt various kinds of shapes. The microparticle sorting apparatus 1 roughly includes at least the discharge direction confirming section 12, opposite electrodes 13a and 13b, an opposite electrode position controlling section 14, a droplet generating section 15, and a charging section 16. In addition, the microparticle sorting apparatus 1 can also include acceptors 17, an acceptor position controlling section 18, and the like as may be necessary. Hereinafter, these constituent elements of the microparticle sorting apparatus 1 will be described in detail.

(1) Flow Path 11

The flow path 11 having the discharge outlet 111 adapted to adopt the various kinds of shapes can be applied to the microparticle sorting apparatus 1 according to the first embodiment. That is to say, even in the case of the flow path 11 in which the shape of the discharge outlet 111 is not fixed due to mass production or the like, and thus a discharge direction of a discharged liquid discharged from the flow path 11 may not be estimated, when the microparticle sorting apparatus 1 according to the first embodiment is used, the microparticles discharged from the flow path 11 can be precisely sorted.

The microparticles are caused to flow through the flow path 11, and a droplet D containing therein the microparticles is discharged from the discharge outlet 111. In the flow path 11, for example, as will be described later, in the case or the like where the microparticle sorting apparatus 1 according to the first embodiment is used in a flow cytometer 10, various kinds of optical information are detected in a predetermined portion.

Figure 2:
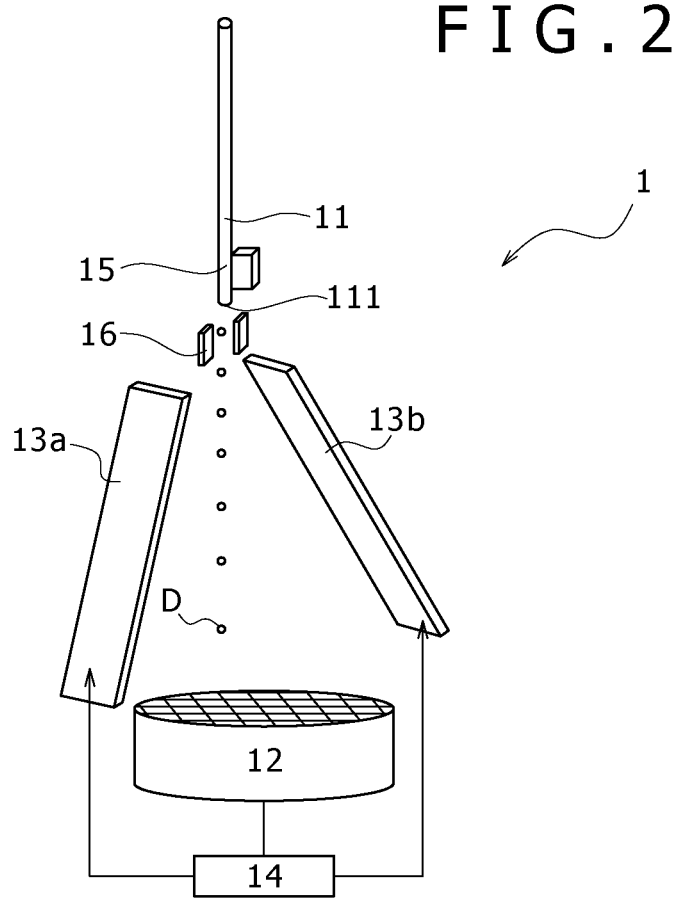
FIG. 2 is a schematic conceptual view schematically showing a microparticle sorting apparatus according to a first change of the first embodiment.

A form of the flow path 11 capable of being applied to the microparticle sorting apparatus 1 according to the first embodiment is especially by no means limited, and thus the flow path 11 can be freely designed. For example, the flow path capable of being applied to the microparticle sorting apparatus 1 is not limited to the flow path 11 formed within a two-dimensional or three-dimensional substrate T made of a plastic, a glass or the like as shown in FIG. 1A. Thus, as shown in FIG. 2, such a flow path 11 as to be used in the existing flow cytometer can also be used in the microparticle sorting apparatus 1 according to the first embodiment. Here, FIG. 2 is a schematic conceptual view schematically showing the microparticle sorting apparatus according to a first change of the first embodiment.

In addition, a flow path width, a flow path depth, and a cross sectional shape of the flow path 11 are also especially by no means limited and thus can be freely designed as long as the form of the flow path 11 can form a laminar flow. For example, a microflow path having a flow path width of 1 mm or less can also be used in the microparticle sorting apparatus 1 according to the first embodiment. In particular, when the microflow path having the flow path width of about 10 μm to about 1 mm is used, a microparticle sorting method according to a third embodiment which will be described later can be more suitably carried out.

It is noted that when the flow path 11 formed on the substrate T is adopted, the substrate T is preferably made of a material having a transparent property. For example, the reason for that is because in the case or the like where as will be described later, the microparticle sorting apparatus 1 according to the first embodiment is used in a flow cytometer 10, each of the light illumination and the optical detection can be made to be carried out from both sides through the substrate T.

(2) Discharge Direction Confirming Section 12

The discharge direction confirming section 12 is a section for confirming the discharge direction of the discharged liquid discharged from the discharge outlet 111 of the flow path 11. Since in the mass-produced flow path 11 or the like, it may be really impossible to control the precision of the shape of the discharge outlet 111, it may also impossible to estimate the discharge direction of the discharged liquid discharged from the discharge outlet 111. However, since the microparticle sorting apparatus 1 according to the first embodiment is provided with the discharge direction confirming section 12, a control liquid is caused to flow through the flow path 11 before the microparticles are actually sorted, thereby making it possible to confirm the discharge direction of the discharged liquid in advance. As a result, the microparticles can be precisely sorted without losing any of the microparticles.

Figure 3A:
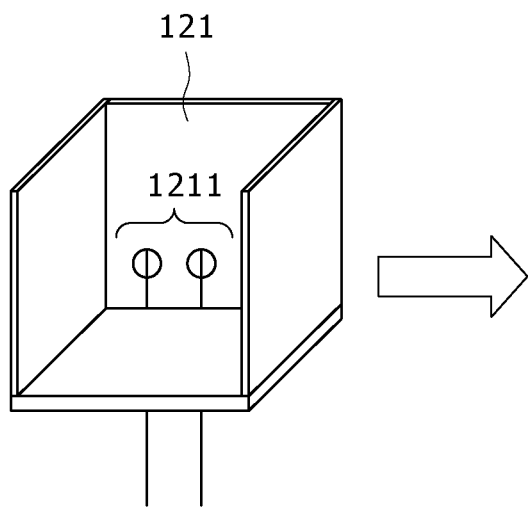
FIGS. 3A and 3B are respectively a schematic conceptual view schematically showing a state in which liquid sensors are installed in each of cells in a discharge direction confirming section, and a state in which invasion of a liquid is sensed by the liquid sensors in the discharge direction confirming section in the microparticle sorting apparatus shown in FIG. 1A.
Figure 3B:
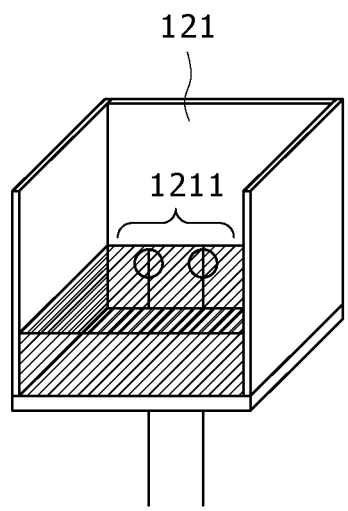

Although the concrete confirming method in the discharge direction confirming section 12 is especially by no means limited as long as the discharge direction of the discharged liquid can be confirmed, for example, it is possible to give a method of confirming the discharge position of the discharged liquid by a liquid sensor. More specifically, there is given a method in which a container is used in which a plurality of cells 121 are formed in a specific pattern (in a lattice in FIG. 1B), liquid sensors 1211 are installed in each of the cells 121 (refer to FIG. 3A), and the invasion of the liquid is sensed by the liquid sensors 1211 (refer to FIG. 3B).

Figure 4:
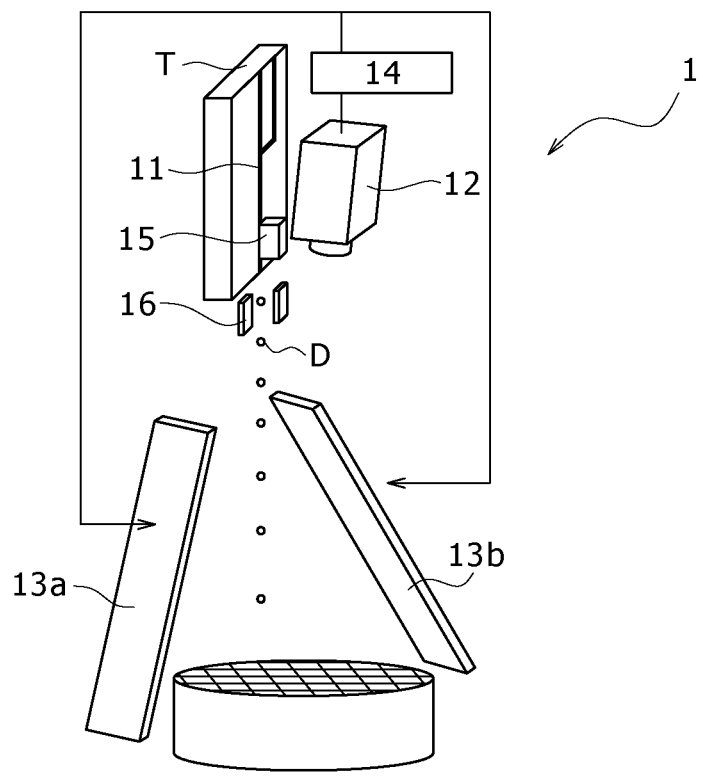
FIG. 4 is a schematic conceptual view schematically showing a microparticle sorting apparatus according to a second change of the first embodiment.

In addition, as shown in FIG. 4, it is also possible to use a method of capturing an image of the discharge position of the discharged liquid. More specifically, a reagent or the like which is adapted to be discolored with a liquid is introduced into each of the insides of the cells 121, and an image of the position of the discolored cell 121, for example, is captured from an upper portion side, thereby making it possible to confirm the discharge position of the discharged liquid. In addition, although not illustrated, the discharged liquid itself is colored without using the container having the cells 121 formed therein, and an image of the discharge direction of the discharged liquid is captured, thereby also making it possible to confirm the discharge position of the discharged liquid.

When the container described above is used, the shape of the pattern formed by a plurality of cells 121 is especially by no means limited and thus can be freely designed as long as the discharge position of the discharged liquid can be confirmed based on the shape concerned. In addition, the image capturing is by no means limited in direction to the image capturing carried out from the upper portion side. For example, although not illustrated, a bottom surface of the container is made of a material having a transparent property, and thus the image capturing can be carried out from the lower portion side.

Figure 5:
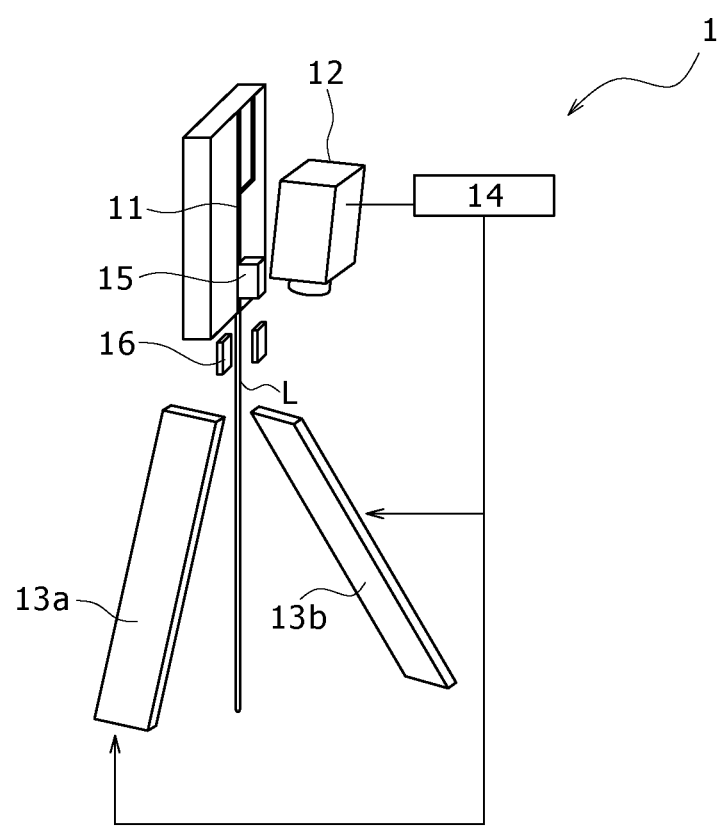
FIG. 5 is a schematic conceptual view schematically showing a microparticle sorting apparatus according to a third change of the first embodiment.

It is noted that when the discharge direction of the discharged liquid is confirmed by the discharge direction confirming section 12, the discharged liquid such as the control liquid is by no means limited to the state in which the droplet D is formed as shown in FIG. 1A to FIG. 4. For example, as shown in FIG. 5, a discharged liquid L is discharged from the discharge outlet 111 of the flow path 11 without forming the droplet D, and the discharge direction of the discharged liquid L may be confirmed by the discharge direction confirming section 12.

(3) Opposite Electrodes 13a and 13b

The opposite electrodes 13a and 13b are discharged downstream with respect to the discharge outlet 111. Also, the opposite electrodes 13a and 13b are a section for changing a traveling direction of the droplet D generated by the droplet generating section 15 which will be described later, containing therein the microparticles and electrically charged by the charging section 16 which will be described later, and sorting the microparticles contained in the droplet D.

A voltage applied across the opposite electrodes 13a and 13b is changed to adjust the strength of an electric repulsion force or attractive force generated between the opposite electrodes 13a and 13b, and the droplet D, thereby making it possible to change the traveling direction of the droplet D to an arbitrary direction.

(4) Opposite Electrode Position Controlling Section 14

The opposite electrode position controlling section 14 is a section for controlling the positions of the opposite electrodes 13a and 13b in accordance with the discharge direction of the discharged liquid confirmed by the discharge direction confirming section 12.

Figure 10A:
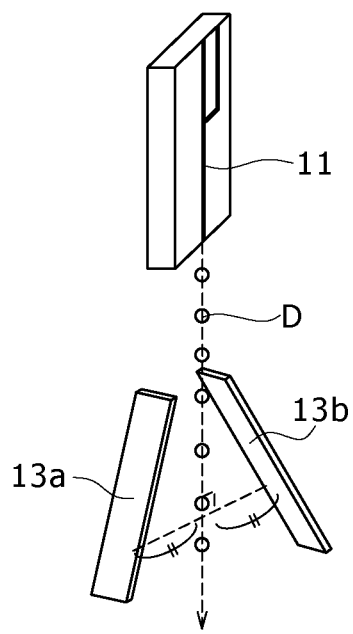
FIGS. 10A and 10B are respectively a schematic conceptual view showing a state in which a discharged droplet discharged from a flow path passes a central portion between opposite electrodes, and a schematic conceptual view showing a state in which the discharged droplet discharged from the flow path diverges sharply from the central portion between the opposite electrodes.
Figure 10B:
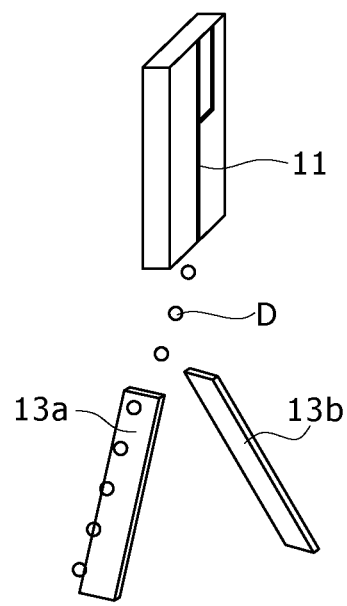

For the purpose of precisely sorting the microparticles contained in the droplet D by using the opposite electrodes 13a and 13b in the manner as described above, the droplet D discharged from the flow path 11 has to be discharged toward the central portion between the opposite electrodes 13a and 13b (refer to FIG. 10A). The reason for this is because when the droplet D is discharged in the direction of sharply diverging from the opposite electrodes 13a and 13b, it may be impossible to change the traveling direction of the droplet D to the desired direction when the voltage is applied across the opposite electrodes 13a and 13b.

Then, in the microparticle sorting apparatus 1 according to the first embodiment, the positions of the opposite electrodes 13a and 13b are controlled by the opposite electrode position controlling section 14 in accordance with the discharge direction of the discharged liquid. The positions of the opposite electrodes 13a and 13b are controlled by the opposite electrode position controlling section 14 in advance, whereby the droplet D containing therein the microparticles can be discharged toward the center between the opposite electrodes 13a and 13b. As a result, even when the flow path 11 having the discharge outlet 111 having any shape, the microparticles contained in the droplet D can be precisely sorted without losing any of the microparticles.

The positions of the opposite electrodes 13a and 13b can be changed to all positions by an up and down movement or a right and left movement as well as a rotational movement as shown in FIG. 1A by a broken line in accordance with the discharge direction of the discharged liquid. It is noted that although it is possible to confirm that the discharge direction of the discharged liquid is directed toward the center between the opposite electrodes 13a and 13b from the beginning depending on the flow path 11 used, in such a case, the positions of the opposite electrodes 13a and 13b are controlled by the opposite electrode position controlling section 14 so as not to be changed.

(5) Droplet Generating Section 15

The droplet generating section 15 is a section for generating the droplet D from the discharge outlet 111 described above. The microparticles in interest are caused to flow through the flow path 11 after the positions of the opposite electrodes 13a and 13b are controlled by the opposite electrode position controlling section 14. The droplets D are generated by the droplet generating section 15 so as to contain therein the microparticles a given amount by a given amount.

A concrete droplet generating method in the droplet generating section 15 is especially by no means limited, and thus any of the known methods can be freely selected to be used. For example, a vibration is applied to all of or a part of the flow path 11 by using a vibration element which vibrates at a predetermined vibration frequency, or the like, thereby making it possible to generate the droplet from the discharge outlet 111 of the flow path 11. It is noted that in this case, the vibration element used is especially by no means limited, and thus any of the known vibration elements can be freely selected to be used. A piezo-vibration element or the like can be given as an example of the vibration element.

With the droplet generating section 15, an amount of liquid caused to flow through the flow path 11, a diameter of the discharge outlet 111, a frequency vibration of the vibration element, and the like are adjusted, thereby making it possible to generate the droplets D so as to contain therein the microparticles a given amount by a given amount.

(6) Charging Section 16

The charging section 16 is a section for electrically charging the droplet D generated by the droplet generating section 15 with the electric charges. With the charging section 16, the voltage is supplied to the entire sheath flow by using a piezoelectric element or the like right before the droplet D is generated, and in the next instant, the electrically charged droplet D is generated. When the piezoelectric element releases the voltage supply, the sheath flow discharges the electric charges through the ground.

For example, in the case or the like where the microparticle sorting apparatus 1 according to the first embodiment is used in the flow cytometer 10 according to the second embodiment, information about the size, the form, the internal structure and the like of each of the microparticles being moved through the flow path 11 is acquired, and the charging section 16 electrically charges the droplet D with the plus or minus electric charges in accordance with the information thus acquired.

The pathway of the droplet D thus electrically charged is changed to the desired direction by the opposite electrodes 13a and 13b across which the voltage is applied, thereby sorting the microparticles contained in the droplet D.

(7) Acceptor 17

Figure 6:
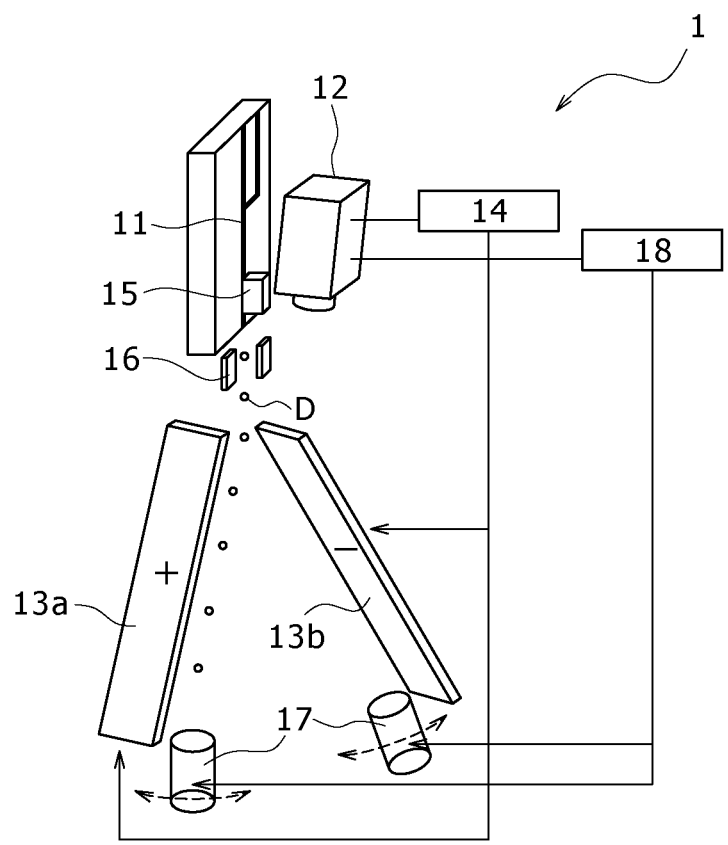
FIG. 6 is a schematic conceptual view schematically showing a microparticle sorting apparatus according to a fourth change of the first embodiment.

The acceptor 17 is used in order to accommodate therein the droplet D (refer to FIG. 6). The form of the acceptor 17 is especially by no means limited and thus can be freely designed as long as the acceptor 17 having such a form can accommodate therein the droplet D containing therein the microparticles. Thus, collection tubes or the like can be individually used, or the container in which a plurality of cells 121 are formed in a specific pattern, or the like such as the container used in the discharge direction confirming section 12 described above can also be used.

(8) Acceptor Position Controlling Section 18

The acceptor position controlling section 18 is a section for controlling the positions of the acceptors 17 in accordance with the movement direction of the droplet D which is moved by the opposite electrode 13a and 13b across which the voltage is applied. Since the microparticle sorting apparatus according to the first embodiment is provided with the opposite electrode position controlling section 14, even though the positions of the acceptors 17 are not controlled, the microparticles contained in the droplet D can be precisely sorted by controlling the positions of the opposite electrodes 13a and 13b. However, it is also estimated that the droplet D is moved to the unexpected position depending on the strength of the voltage applied across the opposite electrodes 13a and 13b. Thus, for carrying out a more precise sorting, the microparticle sorting apparatus 1 according to the fourth change of the first embodiment is provided with the acceptor position controlling section 18, whereby the positions of the acceptors 17 can be controlled in accordance with the movement direction of the droplet D which is moved by the opposite electrodes 13a and 13b across which the voltage is applied.

The positions of the acceptors 17 can be changed to all positions by an up and down movement or a right and left movement as well as a rotational movement as shown in FIG. 6 by a broken line. It is noted that the positions of the acceptors 17 do not have to be changed depending on the flow path 11 used or the strength of the voltage applied across the opposite electrodes 13a and 13b in some cases, in such cases, the positions of the acceptors 17 are controlled by the acceptor position controlling section 18 so as not to be changed.

2. Flow Cytometer 10

Figure 7:
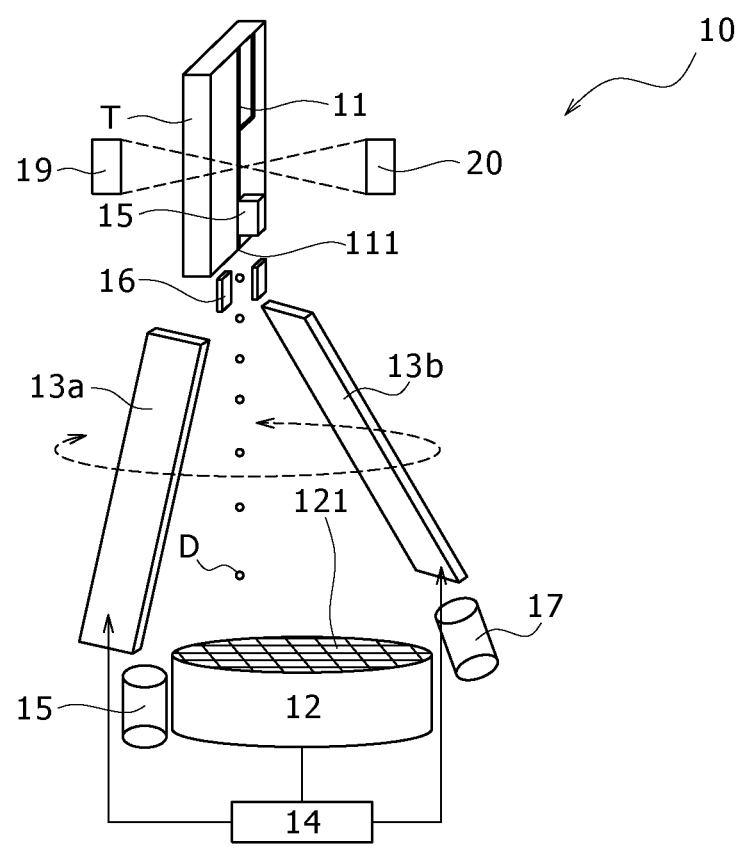
FIG. 7 is a schematic conceptual view schematically showing a flow cytometer according to a second embodiment.

The microparticle sorting apparatus 1 according to the first embodiment can be suitably used in the flow cytometer by utilizing the high sorting precision. FIG. 7 is a schematic conceptual view schematically showing a construction of the flow cytometer 10 according to the second embodiment.

The flow path 11 having the discharge outlet 111 adapted to adopt various kinds of shapes can be applied to the flow cytometer 10 according to the second embodiment. The flow cytometer 10 roughly includes at least the discharge direction confirming section 12, the opposite electrodes 13a and 13b, the opposite electrode position controlling section 14, a light radiating section 19, an optical detecting section 20, the droplet generating section 15, and the charging section 16. In addition, the flow cytometer 10 can also include the acceptors 17, the acceptor position controlling section 18, and the like as may be necessary. Hereinafter, these constituent elements of the flow cytometer 10 according to the second embodiment will be described in detail. It is noted that since the flow path 11 capable of being applied to the flow cytometer 10, the discharge direction confirming section 12, the opposite electrodes 13a and 13b, the opposite electrode position controlling section 14, the droplet generating section 15, the charging section 16, the acceptors 17, and the acceptor position controlling section 18 are the same in constructions as those in the microparticle sorting apparatus 1 according to the fourth change of the first embodiment described above, a description thereof is omitted here for the sake of simplicity.

(1) Light Radiating Section 19

The light radiating section 19 is a section for radiating a light to the microparticles in order to acquire the information about the size, the form, the internal structure and the like of each of the microparticles being caused to flow through the flow path 11.

Although a kind of light radiated from the light radiating section 19 to the microparticles is especially by no means limited, for the purpose of reliably generating the fluorescences or the scattered lights from the microparticles, a light is preferable in which a light direction, a wavelength, and a light intensity are each constant. A laser diode, an LED or the like can be given as an example of the light radiating section 19. When the laser diode is used as the light radiating section 19, a kind of laser diode is also especially by no means limited. However, one kind of or two or more kinds of argon ion (Ar) laser, He—Ne laser, dye laser, Cr laser and so on can be combined with one another to be used.

(2) Optical Detecting Section 20

An optical detecting section 20 is a section for detecting optical information generated from the microparticles by radiating the light to the microparticles by the light radiating section 19.

A kind of optical detecting section 20 which can be used in the flow cytometer 10 according to the second embodiment is especially by no means limited as long as the optical information can be detected. Thus, any of the known photodetectors can be freely selected to be adopted. For example, one kind of or two or more kinds of fluorescence measuring instrument, scattered light measuring instrument, transmitted light measuring instrument, reflected light measuring instrument, diffracted light measuring instrument, ultraviolet spectrometer, infrared spectrometer, Raman spectrometer, FRET measuring instrument, FISH measuring instrument, other various spectrum measuring instruments, so-called multi-channel photodetector having a plurality of photodetectors arranged in an array, and the like can be freely combined with one another to be adopted.

In addition, an installation portion of the optical detecting section 20 in the flow cytometer 10 according to the second embodiment is especially by no means limited and thus can be freely designed as long as the optical information generated from the microparticles can be detected. For example, as shown in FIG. 7, the optical detecting section 20 is preferably disposed across the flow path 11 from the light radiating section 19. The optical detecting section 20 is disposed across the flow path 11 from the light radiating section 19, whereby the light radiating section 19 can be disposed with the freer construction.

The optical information acquired from the microparticles by the optical detecting section 20 is converted into an analog electric signal (such as an analog voltage pulse) to be digitized. In addition, the resulting analog electric signal (such as the analog voltage pulse) is amplified with a suitable amplification factor, and is then subjected to analog-to-digital conversion (A/D conversion). After that, a histogram is extracted by using a computer for analysis for the resulting histogram, and various kinds of software based on the resulting numerical data, thereby carrying out the statistical analysis. The droplet D containing therein the microparticles is electrically charged with the plus or minus electric charges by the charging section 16 in accordance with the analysis result, and thus the traveling direction of the droplet D is changed by the opposite electrodes 13a and 13b, thereby sorting the microparticles contained in the droplet D.

3. Microparticle Sorting Method

Figure 8:
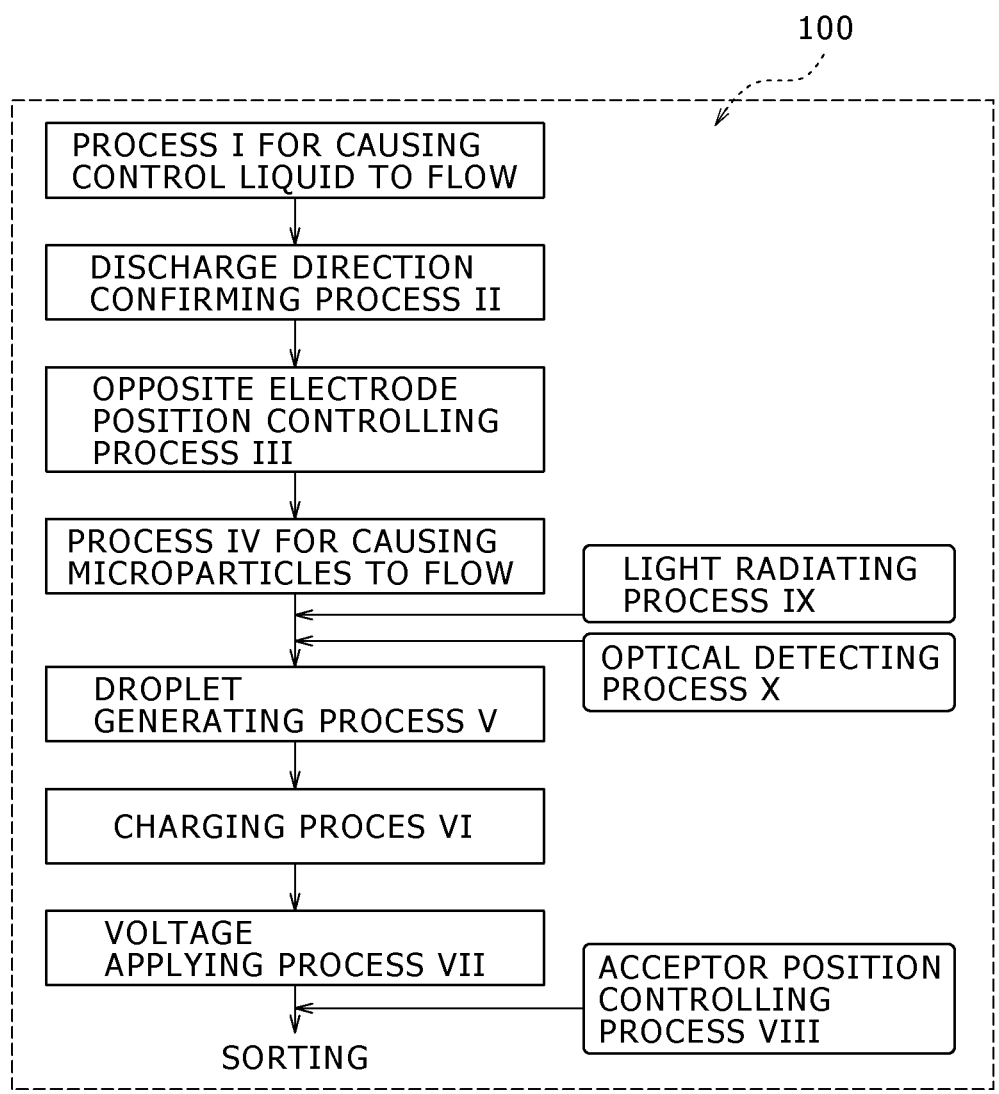
FIG. 8 is a flow chart explaining processes of a microparticle sorting method according to a third embodiment.
Figure 9:
FIG. 9 is a photograph substituted for a drawing when a flow path formed in a plastic substrate is viewed from a flow path outlet (discharge outlet) direction.

FIG. 8 is a flow chart explaining processes in a microparticle sorting method according to a third embodiment.

The microparticle sorting method 100 according to the third embodiment is a method of roughly carrying out at least a process I for causing the control liquid to flow, a discharge direction confirming process II, an opposite electrode position controlling process III, a process IV for causing the microparticles to flow, a droplet generating process V, a charging process VI, and a voltage applying process VII. In addition, the microparticle sorting method 100 according to the third embodiment can also carry out an acceptor position controlling process VIII, a light radiating process IX, and an optical detecting process X as may be necessary. Hereinafter, these processes of the microparticle sorting method 100 according to the third embodiment will be described in detail.

(1) Process for Causing Control Liquid to Flow

The process I for causing the control liquid to flow is a process for causing the control liquid to flow through the flow path 11 in advance before the microparticles as an object of the sorting are caused to flow through the flow path 11 in order to control the positions of the opposite electrodes 13a and 13b in the opposite electrode position controlling process III which will be described later.

The liquid which can be used as the control liquid is especially by no means limited as long as no influence is exerted on causing the microparticles to flow through the flow path 11 which will be described later. For example, water, a sodium chloride solution or the like can be freely selected to be used as the control liquid. In addition, for the purpose of making confirmation of the discharge direction easy in the discharge direction confirming process II which will be described later, the colored control liquid can also be caused to flow through the flow path 11.

(2) Discharge Direction Confirming Process II

The discharge direction confirming process II is a process for confirming the discharge direction of the control liquid discharged from the discharge outlet 111 of the flow path 11. In the mass-produced flow path 11 or the like, it may be really impossible to control the precision of the shape of the discharge outlet 111. Therefore, it may also be impossible to estimate the discharge direction of the control liquid discharged from the discharge outlet 111. However, since the discharge direction confirming process II is carried out in the microparticle sorting method 100 according to the third embodiment, the control liquid is caused to flow through the flow path 11 before the microparticles are actually sorted, thereby making it possible to confirm the discharge direction in advance. As a result, the microparticles can be precisely sorted without losing any of the microparticles.

Although a concrete confirming method in the discharge direction confirming process II is especially by no means limited as long as the discharge direction of the discharged liquid can be confirmed, for example, a method of confirming the discharge position of the control liquid by using a liquid sensor can be given as the concrete confirming method. More specifically, there is given a method in which the container in which a plurality of cells 121 are formed in the specific pattern (refer to FIG. 1B) is used, the liquid sensors 1211 are installed in each of the insides of the cells 121 (refer to FIG. 3A), and the invasion of the liquid is sensed by the liquid sensors 1211 (refer to FIG. 3B).

In addition, as shown in FIG. 4, it is also possible to use a method of capturing the image of the discharge position. More specifically, the reagent or the like which is discolored with the liquid is introduced into each of the insides of the cells 12, and the image of the position of the discolored cell 121, for example, is captured from the upper portion side, thereby making it possible to confirm the discharge position. In addition, although not illustrated, the control liquid itself is colored without using the container having the cells 121 formed therein, and the image of the discharge direction is captured, thereby also making it possible to confirm the discharge position.

When the container described above is used, the shape of the pattern formed by a plurality of cells 121 is especially by no means limited and thus can be freely designed as long as the discharge position can be confirmed based on the shape concerned. In addition, the image capturing is by no means limited in direction to the image capturing carried out from the upper portion side. For example, although not illustrated, the bottom surface of the container is made of the material having the transparent property, and thus the image capturing can be carried out from the lower portion side.

It is noted that when the discharge direction of the control liquid is confirmed in the discharge direction confirming process II, the control liquid is by no means limited to the state in which the droplet D is formed as shown in FIG. 1A to FIG. 4. For example, as shown in FIG. 5, the control liquid L is discharged from the discharge outlet 111 of the flow path 11 without forming the droplet D, and the discharge direction of the control liquid L may be confirmed by the discharge direction confirming process II.

(3) Opposite Electrode Position Controlling Process III

The opposite electrode position controlling process III is a process for controlling the positions of the opposite electrodes 13a and 13b disposed downstream with respect to the discharge outlet 111 in accordance with the discharge direction of the control liquid which is confirmed in the discharge direction confirming process II.

For the purpose of sorting the microparticles contained in the droplet D by using the opposite electrodes 13a and 13b in the manner as described above, the droplet D discharged from the flow path 11 has to be discharged toward the central portion between the opposite electrodes 13a and 13b (refer to FIG. 10A). The reason for this is because when the droplet D is discharged in the direction of sharply diverging from the opposite electrodes 13a and 13b, it may be impossible to change the traveling direction of the droplet D to the desired direction when the voltage is applied across the opposite electrodes 13a and 13b.

Then, in the microparticle sorting method 100 according to the third embodiment, the opposite electrode position controlling process III is carried out to previously control the positions of the opposite electrodes 13a and 13b, whereby the droplet D containing therein the microparticles can be discharged toward the center between the opposite electrodes 13a and 13b. As a result, even when the flow path 11 having the discharge outlet 111 having any shape, the microparticles contained in the droplet D can be precisely sorted without losing any of the microparticles.

The positions of the opposite electrodes 13a and 13b can be changed to all positions by the up and down movement or the right and left movement as well as the rotational movement as shown in FIG. 1A by the broken line in accordance with the discharge direction of the control liquid. It is noted that although it is possible to confirm that the discharge direction of the control liquid is directed toward the center between the opposite electrodes 13a and 13b from the beginning depending on the flow path 11 used, in such a case, in the opposite electrode position controlling process III, the positions of the opposite electrodes 13a and 13b are controlled so as not to be charged.

(4) Process IV for Causing Microparticles to Flow

The process IV for causing the microparticles to flow is a process for causing microparticles to flow through the flow path 11.

Although a method of causing the microparticles to flow through the flow path 11 is especially by no means limited, for example, as with the existing flow cytometry, there is given a method in which a sample flow containing therein the microparticles is carried by a fluid medium (sheath flow) for urging the rectification while the sample flow is held in the fluid medium. Carrying the sample flow in such a manner is more preferably because it is possible to form the laminar flow of the sample flow containing therein the microparticles. Although a kind of fluid medium is especially by no means limited as long as the fluid medium concerned has a function of urging the rectification of the sample flow, for example, the sodium chloride solution or the like can be used when the microparticles are the cells.

In order to allow the optical information to be detected in the light radiating process IX and the optical detecting process X each of which will be described later, the microparticles are preferably modified with a labeling material such as a fluorescent material such as a fluorescent dye, a radioactive material, an intercalator or a micro-beads. For example, when the fluorescent dye is used as the labeling material, a kind of fluorescent dye is especially by no means limited, and thus all the known fluorescent dyes can be used. For example, one kind of or two or more kinds of Cascade Blue, Pacific Blue, Fluorescein isothiocyanate (FITC), Phycoerythrin (PE), Propidium iodide (PI), Texas red (TR), Peridinin chlorophyll protein (PreCP), Allophycocyanin (APC), 4',6-Diamidino-2-phenylindole (DAPI), Cy3, Cy5, Cy7, etc. can be freely combined with one another to be used.

It should be noted that when as with the fluorescent protein, the microparticle itself emits a light, it is unnecessary to modify the microparticles with the labeling material. In addition, when as with the principles of the FRET, a material or the like in which a fluorescent color or the like of the material can be changed by causing an inter-material mutual action to progress within the flow path 11 is used as the microparticle, it is also unnecessary to modify the microparticles with the labeling material.

(5) Droplet Generating Process V

The droplet generating process V is a process for generating the droplets so as to contain therein the microparticles a given amount by a given amount from the discharge outlet 111 of the flow path 11.

A concrete droplet generating method in the droplet generating process V is especially by no means limited, and thus any of the known methods can be freely selected to be used. For example, the vibration is applied to all of or a part of the flow path 11 by using the vibration element which vibrates at the predetermined vibration frequency, thereby making it possible to generate the droplet from the discharge outlet 111 of the flow path 11. It is noted that in this case, the vibration element used is especially by no means limited, and thus any of the known vibration elements can be freely selected to be used. The piezo-vibration element or the like can be given as an example of the vibration element.

With the droplet generating process V, the amount of liquid caused to flow through the flow path 11, the diameter of the discharge outlet 111, the frequency vibration of the vibration element, and the like are adjusted to adjust the size of the droplet D, thereby making it possible to generate the droplets so as to contain therein the microparticles a given amount by a given amount.

(6) Charging Process VI

The charging process VI is a process for electrically charging the droplet D generated in the droplet generating process V with the electric charges.

A concrete charging method in the charging process VI is especially by no means limited, and thus any of the known methods can be freely selected to be used. For example, there is given the method or the like in which the voltage is supplied to the entire sheath flow by using the piezoelectric element right before the droplet D is generated, and in the next instant, the electrically charged droplet D is generated.

In the charging process VI, for example, the droplet D can be electrically charged with the plus or minus electric charges in accordance with the optical information (the information about the size, the form, the internal structure and the like) of the microparticles detected in the light radiating process IX and the optical detecting process X each of which will be described later.

(7) Voltage Applying Process VII

The voltage applying process VII is a process for applying the voltage across the opposite electrodes 13*a* and 13*b* the positions of which are controlled in the opposite electrode position controlling process III. The traveling direction of the droplet D electrically charged with the electric charges in the charging process VI is changed by applying the voltage across the opposite electrodes 13*a* and 13*b*, thereby making it possible to sort the microparticles contained in the droplet D.

In the voltage applying process VII, the voltage applied across the opposite electrodes 13*a* and 13*b* is changed to adjust the strength of the electric repulsion force or attractive force generated between the opposite electrodes 13*a* and 13*b*, and the droplet D, thereby making it possible to change the traveling direction of the droplet D to an arbitrary direction. As a result, the microparticles contained in the droplet D can be sorted.

(8) Acceptor Position Controlling Process VIII

The acceptor position controlling process VIII is a process for controlling the positions of the acceptors 17 in accordance with the movement direction of the droplet D which is moved by the opposite electrode 13*a* and 13*b* across which the voltage is applied. Since in the microparticle sorting method 100 according to the third embodiment, the opposite electrode position controlling process III is carried out, even though the positions of the acceptors 17 are not controlled, the microparticles can be precisely sorted by controlling the positions of the opposite electrodes 13*a* and 13*b*. However, it is also estimated that the droplet D is moved to the unexpected position depending on the strength of the voltage applied across the opposite electrodes 13*a* and 13*b* in the voltage applying process VII. Then, in the microparticle sorting method 100 according to the third embodiment, the acceptor position controlling process VIII is carried out in order to carry out the more precise sorting, whereby the positions of the acceptors 17 can be controlled in accordance with the movement direction of the droplet D which is moved by the opposite electrodes 13*a* and 13*b* across which the voltage is applied.

The positions of the acceptors 17 can be changed to all positions by the up and down movement or the right and left movement as well as the rotational movement as shown in FIG. 6 by the broken line based on the movement direction of the droplet D. It is noted that although the positions of the acceptors 17 do not have to be changed depending on the flow path 11 used or the strength of the voltage applied across the opposite electrodes 13*a* and 13*b* in some cases, in such cases, the positions of the acceptors 17 are controlled by the acceptor position controlling process VIII so as not to be changed.

(9) Light Radiating Process IX

The light radiating process IX is a process for radiating the light to the microparticles in order to acquire the information about the size, the form, the internal structure and the like of each of the microparticles being caused to flow through the flow path 11. Although the light radiating process IX is the process which is not essential to the microparticle sorting method 100 according to the third embodiment, when the microparticles are sorted in accordance with the various kinds of optical information about the microparticles (the information about the size, the form, the internal structure and the like), the light radiating process IX can be carried out while the microparticles in interest are caused to flow through the flow path 11.

Although a kind of light radiated from the light radiating section 19 to the microparticles in the light radiating process IX is especially by no means limited, for the purpose of reliably generating the fluorescences or the scattered lights from the microparticles, the light is preferable in which the light direction, the wavelength, and the light intensity are each constant. The laser diode, the LED or the like can be given as the example of the light radiating section 19. When the laser diode is used as the light radiating section 19, a kind of laser diode is also especially by no means limited. However, one kind of or two or more kinds of argon ion (Ar) laser, He—Ne laser, dye laser, Cr laser and so on can be combined with one another to be used.

(10) Optical Detecting Process X

The optical detecting process X is a process for detecting the optical information generated from the microparticles by radiating the light to the microparticles by the light radiating section 19 in the light radiating process IX. Although the optical detecting process X is the process which is not essential to the microparticle sorting method 100 according to the third embodiment, when the microparticles are sorted in accordance with the various kinds of optical information about the microparticles (the information about the size, the form, the internal structure and the like), the optical detecting process X can be carried out while the microparticles in interest are caused to flow through the flow path 11.

In the optical detecting process X, a method of acquiring the optical information is especially by no means limited as long as the optical information from the microparticles can be detected, and thus any of the known methods can be freely selected to be adopted. For example, one kind of or two or more kinds of fluorescence measuring method, scattered light measuring method, transmitted light measuring method, reflected light measuring method, diffracted light measuring method, ultraviolet spectrometric method, infrared spectrometric method, Raman spectrometric method, FRET measuring method, FISH measuring method, other various spectrum measuring methods, method using a so-called multicolor detecting method capable of detecting a plurality of dyes or the like, and so on can be freely combined with one another to be adopted.

The optical information acquired from the microparticles in the optical detecting process X is converted into the analog electric signal (such as the analog voltage pulse) to be digitized. In addition, the resulting analog electric signal (such as the analog voltage pulse) is amplified with the suitable amplification factor, and is then subjected to the analog-to-digital conversion (A/D conversion). After that, the histogram is extracted by using the computer for analysis, and various kinds of software based on the resulting numerical data, thereby carrying out the statistical analysis for the histogram. The droplet D containing therein the microparticles is electrically charged with the plus or minus electric charges in the charging process VI in accordance with the analysis result, and thus the traveling direction of the droplet D is changed in the voltage applying process VII, thereby sorting the microparticles contained in the droplet D.

According to the present application, even when the flow path having the discharge outlet having any shape is used, the microparticles can be precisely sorted without losing any of the microparticles. For this reason, when the flow path is used which is formed within the substrate made of the plastic, the glass or the like, or the mass-produced flow path is used, that is, even when the shape of the outlet of the flow path is not precisely processed, thereby causing the dispersion in the discharge direction, it is possible to precisely sort the microparticles.

Use of this technique can contribute to the improvement in the analysis and deconvolution technique in the various kinds of fields such as the medical field (such as the pathology, the tumor immunology, the transplantation studies, the genetics, the regenerative medicine, and the chemical care), the drug-discovery field, the clinical laboratory field, the food field, the agriculture field, the engineering field, the forensic medicine field, and the criminal identification field.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microparticle sorting apparatus, comprising:
   discharge direction confirming means for confirming a discharge direction of a discharged liquid discharged from a discharge outlet of a flow path by detecting a contact position of said liquid upon an object;
   opposite electrodes disposed downstream with respect to said discharge outlet;
   opposite electrode position controlling means for controlling positions of said opposite electrodes in accordance with the discharge direction confirmed by said discharge direction confirming means;
   droplet generating means for generating a droplet from said discharge outlet; and
   charging means for electrically charging the droplet with electric charges.

2. The microparticle sorting apparatus according to claim 1, further comprising:
   an acceptor for accommodating the droplet.

3. The microparticle sorting apparatus according to claim 2, further comprising:
   acceptor position controlling means for controlling a position of said acceptor in accordance with a movement direction of the droplet which is moved by said opposite electrodes across which a voltage is applied.

4. The microparticle sorting apparatus according to claim 1, wherein said discharge direction confirming means is means for confirming a discharge position of the discharged liquid by a liquid sensor disposed on the object.

5. The microparticle sorting apparatus according to claim 1, wherein said discharge direction confirming means is means for capturing an image of a discharge position of the discharged liquid upon the object.

* * * * *